United States Patent [19]

Chu et al.

[11] Patent Number: 4,777,268

[45] Date of Patent: Oct. 11, 1988

[54] SELECTIVE OXIDATION OF ALKYLAROMATIC EMPLOYING LAYERED TITANATE CONTAINING INTERSPATHIC SILICA

[75] Inventors: Pochen Chu, West Deptford; Larry A. Green, Michleton; Michael E. Landis, Woodbury, all of N.J.

[73] Assignee: Mobil Oil Corporation, New York, N.Y.

[21] Appl. No.: 26,426

[22] Filed: Mar. 16, 1987

Related U.S. Application Data

[63] Continuation of Ser. No. 879,787, Jun. 27, 1986, which is a continuation-in-part of Ser. No. 687,414, Dec. 28, 1984, abandoned.

[51] Int. Cl.$^4$ ............................................ C07D 307/89
[52] U.S. Cl. ................................................... 549/248
[58] Field of Search ......................................... 549/248

[56] References Cited

U.S. PATENT DOCUMENTS

| | | | |
|---|---|---|---|
| 4,077,984 | 3/1978 | Blechschmitt et al. | 260/346.4 |
| 4,481,304 | 11/1984 | Sato et al. | 502/209 |
| 4,600,503 | 7/1986 | Angevine et al. | 208/251 H |
| 4,650,779 | 3/1987 | Goldstein | 502/38 |

*Primary Examiner*—Richard L. Raymond
*Attorney, Agent, or Firm*—Alexander J. McKillop; Michael G. Gilman; Laurence P. Hobbes

[57] ABSTRACT

A process and catalyst are disclosed for selectively oxidizing alkylaromatics, e.g., o-xylene, to oxygenated aromatics, e.g., phthalic anhydride. The catalyst of the process comprises a layered titanate which contains interspathic polymeric silica and a heavy metal element, e.g., vanadium.

17 Claims, No Drawings

SELECTIVE OXIDATION OF ALKYLAROMATIC EMPLOYING LAYERED TITANATE CONTAINING INTERSPATHIC SILICA

This case is a continuation in part of U.S. application Ser. No. 879,787, filed June 27, 1986 which in turn is a continuation in part of U.S. application Ser. No. 687,414, filed Dec. 28, 1984, now abandoned, the entire contents of these applications being incorporated herein by reference.

This invention relates to a process of converting alkylaromatics, e.g., o-xylene to aromatic oxygenates, e.g., phthalic anhydride by selective oxidation. More particularly, the present invention relates to selective oxidation of o-xylene in the presence of a catalyst comprising a layered titanate containing an interspathic polymeric silica. This invention further relates to the catalysts employed for such selective oxidation.

Phthalic anhydride can be used in preparing alkyl, amino and epoxy resins, as a flame retardant, rubber retarder, or as an ester for plasticizers and polyesters. In 1976 worldwide manufacture of phthalic anhydride exceeded 1.7 million metric tons per annum.

Phthalic anhydride was first commercially prepared from naphthalene by liquid phase oxidation with sulfuric acid in the presence of a mercury catalyst. A greatly improved method was discovered during World War I which employed a vapor phase, catalytic, air oxidation process and was adapted to the oxidation of o-xylene on a commercial scale in 1945.

Two types of fixed bed vapor phase processes have been used to oxidize o-xylene to phthalic anhydride---those employing low temperatures, low space-velocities, and those utilizing high temperature and high space velocities. Because the conversion of o-xylene to phthalic anhydride is highly exothermic, both processes may control heat buildup by using small diameter catalyst tubes surrounded by an efficient heat-exchange medium such as boiling on a molten salt mixture. Alternatively, a fluidized catalyst may be used in tandem with cooling coils in the catalyst bed.

The minimum temperature needed to induce oxidation can vary depending on the catalyst employed. Most catalysts used in this process contain as an active component some form of heavy metal such as vanadium, generally in the form of vanadium pentoxide. Titanium oxide may also be present in the catalyst in order to increase its affinity for oxygen while improving phthalic anhydride selectivity. These active materials can be coated on an inert core, e.g. granular aluminum, to provide a catalyst which permits high feed rates in the reactor while avoiding the formation of excessive heat in the catalyst bed. An example of such a catalyst is disclosed in U.S. Pat. Nos. 4,481,304 and 4,077,984, the entire contents of which are incorporated herein by reference.

Typical by-products of the oxidation of o-xylene include maleic anhydride, carbon dioxide, carbon monoxide, aromatic aldehyde, benzoic and toluic acids, phthalide, acrolein and alpha-methyl acrolein. In general, the proportion of phthalide and aldehydes increases at low temperatures and low air/hydrocarbon ratios while maleic anhydride and carbon oxides increase at higher temperatures air/hydrocarbon ratios.

Phthalic anhydride can be recovered from the converter effluent in various ways, including condensation as a solid in large air-cooled vessels or by scrubbing the phthalic anhydride-containing gases from the catalytic converter with water in order to hydrate the anhydride to the acid, which precipitates from solution forming an aqueous slurry. The acid can then be separated by filtration or centrifugation and dehydrated to reform the anhydride.

It has now been found that catalysts containing thermally stable silicotitanate, i.e., layered titanate containing interspathic polymeric silica, can selectively oxidize o-xylene to a product rich in phthalic anhydride when said catalysts contain a heavy metal selected from the group consisting of Cu, Ga, Co, Mn, Ni, Fe, Cr, V, Mo, W, Sn and Ce. A reaction mixture comprising o-xylene and oxygen is contacted under partial oxidation conditions with such a catalyst which contains at least one of the heavy metal elements, preferably vanadium in the form of $V_2O_5$. The catalyst should contain about 0.1 to 20 weight percent of said heavy metal element, preferably about 1 to 5 weight percent.

The heavy metal element can be incorporated into the silicotitanate by any suitable known method such as ion exchange or impregnation. Ion exchange is particularly useful where the silicotitanate contains residual sodium associated with the titanate framework.

Many layered materials are known which have three-dimensional structures which exhibit their strongest chemical bonding in only two dimensions. In such materials, the stronger chemical bonds are formed in two-dimensional planes and a three-dimensional solid is formed by stacking such planes on top of each other. However, the interactions between the planes are weaker than the chemical bonds holding an individual plane together. The weaker bonds generally arise from interlayer attractions such as Van der Waals forces, electrostatic interactions, and hydrogen bonding. In those situations where the layered structure has electronically neutral sheets interacting with each other solely through Van der Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction mediated by ions located between the layers. In addition, hydrogen bonding interactions can occur directly between complementary sites on adjacent layers, or can be mediated by interlamellar bridging molecules.

Laminated materials such as clays may be modified to increase their surface area. In particular, the interlamellar spacing can be increased substantially by absorption of various swelling agents such as water, ethylene glycol, amines, ketones, etc. which enter the interlamellar space and push the layers apart. However, the interlamellar spaces of such layered materials tend to collapse when the molecules occupying the space are removed, for example, by exposing the clays to high temperatures. Accordingly, such layered materials having enhanced surface area are not suited for use in chemical processes involving even moderately severe conditions.

The extent of interlayer separation can be estimated by using standard techniques such as X-ray diffraction to determine the basal spacing, also known as "repeat distance" or "d-spacing." These values indicate the distance between, for example, the uppermost margin of one layer with the uppermost margin of its adjoining layer. If the layer thickness is known, the interlayer spacing can be determined by subtracting the layer thickness from the basal spacing.

The silicotitanate of the present invention has a substantially uniform interlayer distance sufficiently large to permit entry of o-xylene molecules as well as to permit exit of phthalic anhydride therefrom. Generally, the interlayer distance may range from about 1 to 30 or more angstroms, preferably about 6 to 20 angstroms.

The present invention may utilize a catalyst prepared from a layered titanate starting material which contains ion exchange sites having interspathic cations associated therewith. Such interspathic cations may include hydrogen ion, hydronium ion and alkali metal cation. The starting material is treated with a "propping" agent comprising a source of organic cation such as organoammonium ion in order to effect an exchange of the interspathic cations resulting in the layers of the starting material being propped apart. The source of organic cations in those instances where the interspathic cations include hydrogen or hydronium ions may include a neutral compound such as organic amine which is converted to a cationic analogue under such conditions. The organic cation should be capable of displacing or supplanting the original interspathic cations. The foregoing treatment results in the formation of a layered metal oxide of enhanced interlayer separation depending upon the size of the organic cation introduced.

After the ion exchange, the organic-"propped" species is treated with a compound capable of forming interspathcic polymeric silica. Preferably, such compounds are capable of forming the polymeric silica upon hydrolysis. It is preferred that the organic cation deposited between the layers be capable of being removed from the layered oxide material without substantial disturbance or removal of the interspathic polymeric silica. For example, organic cations such as n-octylammonium may be removed by exposure to calcination or chemical oxidation conditions, preferably after the interspathic polymeric silica precursor has been converted to the polymeric silica.

The polymeric silica precursor-containing product is exposed to suitable conversion conditions, such as hydrolysis and/or calcination to form the layered material employed in the present invention. The hydrolysis step may be carried out by any method, for example, by interspathic water already present in organic "propped" layered oxide material. Because of the effect of interspathic water on hydrolysis, the extent of hydrolysis may be modified by varying the extent to which the organic-"propped" species is dried prior to addition of the polymeric silica precursor. As noted earlier, the product after conversion to the polymeric silica form may be exposed to conditions which remove the organic cation propping agents, e.g., exposure to elevated temperature.

The amount of interspathic polymeric silica contained within the final product can be greatly varied because the polymeric oxide precursor species are introduced in an electrically neutral form such that the amount of interspathic material incorporated within the layered titanate is not dependent upon the charge density of the original layered titanate. This allows the formation of materials with widely varying interlayer spacing, which permits accommodation of metal-containing molecules through the layered titanate.

The resulting product may have d-spacings greater than 10, 15, 20, 25 or even 30 angstroms. In particular, layered trititanates like $Na_2Ti_3O_7$ are useful starting materials. The starting materials generally comprise an interspathic cationic species between their layers. Trititanate is a commercially available material whose structure consists of infinite anionic sheets of titanium octahedra with intercalated alkali metal cations. The layered metal oxide component contains a stable polymeric oxide, preferably silica, between adjoining layers resulting in a heat-stable material which substantially retains its interlayer distance upon calcination. Silicotitanates prior to incorporation of the heavy metal element, exhibit the characteristic X-ray diffraction pattern of Table 1 below.

TABLE 1

| | Composite List of Principal X-Ray Powder* Diffraction Peaks for Silicotitanates | | |
|---|---|---|---|
| Line Number | 2 Theta Minimum | 2 Theta Maximum | $100/I/I_o$ (Relative Intensity) Range |
| 1 | less than or equal to 8.7 | | VS to W |
| 2 | 11.1–14.3 | | S to W |
| 3 | 11.8–15.2 | | M to W |
| 4 | 24.5–25.0 | | VS to W |
| 5 | 25.0–25.4 | | M to W |
| 6 | 28.5–30.2 | | VS to W |
| 7 | 29.8–30.6 | | S to W |
| 8 | 33.0–33.5 | | S to W |
| 9 | 43.2–43.5 | | M to W |
| 10 | 44.2–44.7 | | M to W |
| 11 | 48.5–48.9 | | VS to M |
| 12 | 52.7–52.9 | | W |

*Theta minimum–2 Theta maximum = Range of 2 Theta-values observed for eight specific pillared silicotitanates These values were determined by standard techniques. The radiation was the K-alpha doublet of copper, and a scintillation counter spectrometer was used. The peak heights, I, and the positions as a function of 2 times theta, where theta is the Bragg angle, were determined. From these, the relative intensities, $I/I_o$ where $I_o$ is the intensity of the strongest line or peak, and d is the interplanar spacing in angstroms (A), corresponding to the recorded lines, were calculated. The relative intensity in the table above is expressed as follows:

| Relative Intensity | 100 $I/I_o$ |
|---|---|
| VS (Very strong) | 60–100 |
| S (Strong) | 40–60 |
| M (Medium) | 20–40 |
| W (Weak) | 0–20 |

Variations in the interplanar spacing and relative intensity may occur as a result of ion exchange, changes in the composition of the silicotitanate, or exposure to calcination conditions.

The polymeric silica precursor employed may be an electrically neutral, hydrolyzable compound, such as tetrapropylorthosilicate, tetramethylorthosilicate, or preferably tetraethylorthosilicate.

The starting layered titanate is treated with an organic compound capable of forming cationic species such as organophosphonium or organoammonium ion, before adding the polymeric oxide source. Insertion of the organic cation between the adjoining layers serves to separate the layers in such a way as to make the layered titanate receptive to the interlayer addition of the electrically neutral, hydrolyzable, polymeric silica precursor. In particular, alkylammonium cations have been found useful in the present invention. $C_3$ and larger alkylammonium, e.g., n-octylammonium is readily incorporated within the interlayer species of the layered oxides, serving to prop open the layer in such a way as to admit the polymeric silica precursors. The extent of the interlayer spacing can be controlled by the size of the organoammonium ion employed. Indeed, the size and shape of the ammonium ion can affect whether or not the organoammonium ion can be interspathically incorporated within the layered oxide structure at all. For example, bulky cations such as tetrapropylammonium are not particularly suited to the present invention.

The organic ammonium cation precursor may be formed by combining a precursor amine and a suitable acid. e.g., mineral acids such as hydrochloric acid. The layered titanate starting material can then be combined with the resulting aqueous solution of ammonium ion to form a layered oxide containing intercalated organic material and water. The resulting "propped" product is then contacted with an electrically neutral, hydrolyzable polymeric silica precursor. After hydrolysis, preferably by exposure to interspathic water, the polymeric silica precursor forms a thermally stable polymeric silica. A final calcination step may be employed which is severe enough to remove the organic interspathic species. Remaining organic may also be removed, if desired, by a separate chemical treatment.

The resulting layered titanate material is contacted with a source of an element selected from the group consisting of Cu, Ga, Co, Mn, Ni, Fe, Cr, V, Mo, W, Sn and Ce. This source of heavy metal is preferably in the form of a metal oxide or a metal salt such as ammonium, oxalate, formate, acetate, tartate or salicylate which can be converted to a metal oxide on heating. Vanadium is preferably added in the form of vanadium pentoxide, $V_2O_5$. The source of heavy metal element is mixed with the layered titanate material before or preferably after incorporation of interspathic polymeric silica, in the presence of water or an organic solvent, e.g., formamide, ammonium thiocyanate, molten urea or an alkanol. The resulting product contains anywhere from about 0.1 to 20 weight percent, preferably about 1 to 5 weight percent of said heavy metal element or elements and is formed into granules or extrudates for proper handling. Surface area may vary from about 10 to 500 $m^2/g$, preferably about 20 to 200 $m^2/g$.

An inorganic oxide binder may be added to the silicotitanate catalyst composition either before or preferably after incorporation of the heavy metal element so that the resulting catalyst comprises about 1 to 99 weight percent, preferably about 5 to 50 weight percent of inorganic oxide binder. Tabular alumina of the same particle size as the silicotitanate composition is particularly suited for compositing the silicotitanate of the present invention. After compositing, the catalyst may have an overall surface area of about 1 to 400, preferably about 5 to 200 $m^2/g$ The resulting catalyst is used to prepare phthalic anhydride from o-xylene by contacting a reaction mixture comprising o-xylene in the presence of oxygen under partial oxidation conditions. These conditions comprise a temperature of about 100° to 500° C., preferably about 200° to 350° C., a pressure of about 0 to 500 psig, preferably about 0 to 100 psig, and an LHSV of about 0.1 to 20, preferably about 0.2 to 5.0. Oxygen and o-xylene are added to the reaction mixture in a ratio of about 5 to 20.

Other alkylaromatics can be oxidized under the same conditions employed for selective oxidation of o-xylene. Toluene can be converted to terepthalic acid in a two-step oxidation process which first selectively converts toluene to p-tolualdehyde over the catalyst of the present invention in the presence of carbon monoxide. p-Tolualdehyde is then converted to terepthalic acid over the same catalyst in the presence of oxygen. Toluene can be directly converted to benzoic acid in the presence of the catalyst and oxygen. p-Xylene can be oxidized to p-toluic acid over the catalyst of the present invention in the process of oxygen. P-Xylene can also be converted to dimethylterephthalate by oxidation over the catalyst of the present invention in the presence of oxygen followed by methylation in the presence of methanol.

The following examples are cited to illustrate more specifically the preparation and use of the catalysts of this invention, but are not to be construed as limiting in scope.

Example 1

One kg of $Na_2Ti_3O_7$ was exchanged in triplicate with 16 liters of 1.0 M HCl with stirring at 170° C. for 24 hours. The solid was filtered and washed with 4 liters of water after the first two exchanges. After the third exchange, the product was filtered, washed chloride-free with water and dried at 77° C. for one hour in vacuo. A mixture of 700 g of this material in 700 g of octylamine and 10.5 liters of water was refluxed with stirring for 23 hours. The product was filtered, washed with 10 liters of hot water, and dried at room temperature for 3 days. 600 g of this product were stirred in 4 kg of tetraethylorthosilicate for 67 hours at room temperature, filtered, and then dried for 24 hours at room temperature. 800 g of the dried product were calcined in $N_2$ at 510° C. for 2 hours and in air for one hour at 510° C. The final silicotitanate product had a surface area of 394 $m^2/g$ and the following composition (wt %):

| | |
|---|---|
| $TiO_2$ | 65.2 |
| $SiO_2$ | 37.3 |
| Na | 0.34 |
| Ash | 97.61 |

EXAMPLE 2

A mixture of 900 g $Na_2Ti_3O_7$, 770 g n-octylamine, 559 g 37.8% HCl and 5 liters of water was refluxed for 22 hours. The solution was cooled to 70° C. and 281 g of 37.8% HCl were added. The product was filtered, washed with 10 liters of hot water, and dried 20 hours at room temperature. The solid product was stirred in 3 liters of absolute ethanol at room temperature for one hour, filtered, and air-dried at room temperature for 24 hours. This material was then stirred in 4 liters of water at room temperature for 23 hours, filtered, and dried for 24 hours at room temperature. 825 g of the dried product were mechanically stirred in 5.5 kg of tetraethylorthosilicate in a 10 liter beaker covered with perforated aluminum foil for 68 hours at room temperature and then filtered and dried in air at room temperature for about 4 days. This material was calcined in nitrogen at 510° C. for 2 hours and then in air for one hour at 510° C. The silicotitanate product had a surface area of 200 $m^2/g$ and the following composition (wt %):

| | |
|---|---|
| $TiO_2$ | 70.2 |
| $SiO_2$ | 21.7 |
| Na | 3.3 |

| -continued | |
|---|---|
| Ash | 100.0 |

EXAMPLE 3

Ten grams of the product from Example 1 were treated with a solution of 0.7 g $V_2O_5$ and 0.7 g oxalic acid in 50 g of water. The mixture was stirred for one hour and dried in a vacuum oven for 16 hours at about 80° C. The dried product was sized to 14/25 mesh and calcined in air at 482° C. for 16 hours. The final product had a surface area of 184 $m^2/g$.

EXAMPLE 4

Ten grams of product from Example 2 were treated with a solution of 0.7 g of $V_2O_5$, 0.7 g oxalic acid and 50 g of $H_2O$. The mixture was stirred for one hour then dried in a vacuum oven for 16 hours at about 80° C. The dried product was sized to 14/25 mesh and calcined in air at 482° C. for 16 hours. The final product had a surface area of 137 $m^2/g$.

EXAMPLE 5

One volume of the catalyst described in Example 3 was blended with 2 volumes of 14/25 mesh tabular alumina. One milliliter of the resulting catalyst mixture was charged to a small glass reactor of 9.5 mm internal diameter with an imbedded thermocouple. o-Xylene at 0.2 ml/hr and air at 50 ml/min rate were charged into the reactor down-flow. The reaction temperature was set at about 315° C. Products (solid, hydrocarbon and aqueous phases) were collected over wet ice. Gaseous products were not collected. The recovery was 60-65% on a weight basis. The conversion and C oxygenates selectivities are provided in Table 2. A similar test was also carried out over the catalyst prepared in Example 4; results are likewise provided in Table 2.

EXAMPLE 6

An aqueous solution was prepared by dissolving 1.4 g $V_2O_5$ and 1.4g oxalic acid in 100 g of water. Twenty grams of $TiO_2$ in the anatase form were added to the solution with agitation. After one hour the mixture was dried in a vacuum over for 22 hours. The dried sample was then calcined in air at 900° F. for 16 hours. The catalyst was found to have 3.3% V by weight and 6 $m^2/g$ surface area.

EXAMPLE 7

The procedure of Example 6 was repeated except that $TiO_2$ of rutile form was used. The catalyst contained 3.1% V and had a surface area of less than 5 $m^2/g$.

EXAMPLE 8

The catalysts from Examples 6 and 7 were tested according to the procedures and conditions of Example 5. The results are listed in Table 2.

The results from these experiments indicate that the $V_2O_5$ on the low sodium silicotitanate from Example 1 is active and selective for oxidation of o-xylene to phthalic anhydride. Selectivity is greater for the silicotitanate than for $V_2O_5$ on rutile, $TiO_2$ under these conditions.

TABLE 2

| | Partial Oxidation Product Distribution | | | |
|---|---|---|---|---|
| Catalyst | Ex. 3 | Ex. 4 | Ex. 6 | Ex. 7 |
| Temp., °F. | 600 | 600 | 600 | 600 |
| Conversion, % (partial oxidation) | 12.5 | 6.7 | 17.8 | 11.2 |
| Non-aqueous Recovered Product Distribution | | | | |
| Phthalic Anhydride | 87.9 | 48.6 | 63.6 | 25.0 |
| Tolualdehyde | 10.1 | 45.9 | 16.6 | 45.7 |
| Methyl Benzoic Acid | 1.0 | 2.0 | 2.0 | 6.7 |
| Phthalide | 1.0 | 3.5 | 17.8 | 22.6 |

We claim:

1. A method for selectively oxidizing alkylaromatics to form a product rich in aromatic oxygenates which comprises contacting a reaction mixture comprising alkylaromatics in the presence of oxygen under partial oxidation conditions with a catalyst comprising a layered titanate composition having a d-spacing of at least about 10 angstroms and prepared from a layered trititanate, which contains interspathic polymeric silica, said catalyst having incorporated therein about 0.1 to 20 weight percent of an element selected from the group consisting of Co, Mn, Ni, Fe, Cr, V, Mo, W, Sn and Ce.

2. A method for selectively oxidizing o-xylene to form a product rich in phthalic anhydride which comprises contacting a reaction mixture comprising o-xylene in the presence of oxygen under partial oxidation conditions with a catalyst comprising a layered titanate composition having a d-spacing of at least about 10 angstroms and prepared from a layered trititanate, which contains interspathic polymeric silica, said catalyst having incorporated therein about 0.1 to 20 weight percent of an element selected from the group consisting of Co, Mn, Ni, Fe, Cr, V, Mo, W, Sn and Ce.

3. The method of claim 2 wherein said partial oxidation condistions comprise a temperature of about 100° to 500° C., a pressure of about 0 to 200 psig, an LHSV of about 0.1 to 20 and said oxygen and o-xylene being added to the reaction mixture in a ratio of about 1 to 50 moles of oxygen per mole of o-xylene.

4. The method of claim 3 wherein said oxidation conditions comprise a temperature of 200° to 400° C., a pressure of about 0 to 100 psig, an LHSV of about 0.2 to 10 and a ratio of about 5 to 20 moles of oxygen per mole of o-xylene.

5. The method of claim 2 wherein said layered titanate composition is prepared from a silicotitanate having the X-ray diffraction pattern set out in Table 1 prior to incorporation of said element.

6. The method of claim 2 wherein said element is selected from the group consisting of V and Cr.

7. The method of claim 2 wherein said layered titanate composition is prepared by swelling a layered trititanate with an alkylamine, contacting the swelled trititanate with a tetraalkylorthosilicate to introduce oxides of silicon between the layers of said trititanate, exposing the resulting trititanate to hydrolysis conditions and thereafter contacting the layered titanate with a source of an element selected from the group consisting of V and Cr.

8. The method of claim 7 wherein said layered trititanate is $Na_2Ti_3O_7$, said alkylamine is n-octylamine, said tetraalkylorthosilicate is tetraethylorthosilicate and said element is V.

9. The method of claim 7 wherein said layered trititanate is hydrogen-exchanged prior to said swelling.

10. The method of claim 8 wherein said layered trititanate is hydrogen exchanged prior to said swelling.

11. The method of claim 2 wherein said catalyst comprises about 0.1 to 90 weight percent of an inorganic binder.

12. The method of claim 2 wherein said catalyst comprises about 0.1 to 90 weight percent alumina binder.

13. The method of claim 1 wherein said element is incorporated within the layers of said layered titanate composition by ion exchange.

14. The method of claim 2 wherein said element is incorporated within the layers of said layered titanate composition by impregnation.

15. The method of claim 2 wherein said element is obtained from vanadium oxalate.

16. The method of claim 2 wherein said o-xylene is present in substantially liquid phase.

17. The method of claim 2 wherein said o-xylene is present in substantially vapor phase.

* * * * *